(12) United States Patent
Wagner (10) Patent No.: US 8,266,795 B2
(45) Date of Patent: Sep. 18, 2012

(54) METHODS OF MAKING AN ELECTROCHEMICAL GAS SENSOR

(75) Inventor: Mark Wagner, Clarence, NY (US)

(73) Assignee: Sensorcon, Inc., Buffalo, NY (US)

( * ) Notice: Subject to any disclaimer, the term of this patent is extended or adjusted under 35 U.S.C. 154(b) by 366 days.

(21) Appl. No.: 12/446,896

(22) PCT Filed: Oct. 22, 2007

(86) PCT No.: PCT/US2007/082077
§ 371 (c)(1),
(2), (4) Date: Aug. 6, 2009

(87) PCT Pub. No.: WO2008/057744
PCT Pub. Date: May 15, 2008

(65) Prior Publication Data
US 2009/0301876 A1 Dec. 10, 2009

(51) Int. Cl.
*H05K 3/44* (2006.01)
*H05K 3/30* (2006.01)
*H05K 5/00* (2006.01)
*C25C 7/02* (2006.01)
*B29C 45/00* (2006.01)
*G01N 27/26* (2006.01)

(52) U.S. Cl. ............... 29/847; 29/848; 29/846; 29/854; 29/825

(58) Field of Classification Search ............ 29/825–853
See application file for complete search history.

(56) References Cited

U.S. PATENT DOCUMENTS

| 3,728,787 A | * | 4/1973 | McDonough | 29/877 |
|---|---|---|---|---|
| 4,227,984 A | | 10/1980 | Dempsey et al. | 204/195 S |
| 4,587,003 A | | 5/1986 | Tantram et al. | 204/412 |
| 4,874,500 A | | 10/1989 | Madou et al. | 204/412 |
| 5,126,035 A | | 6/1992 | Kiesele et al. | 204/415 |
| 5,173,166 A | | 12/1992 | Tomantschger et al. | 204/412 |
| 5,192,415 A | * | 3/1993 | Yoshioka et al. | 204/403.08 |
| 5,228,974 A | | 7/1993 | Kiesele et al. | 204/415 |
| 5,302,274 A | | 4/1994 | Tomantschger et al. | 204/412 |
| 5,304,293 A | * | 4/1994 | Tierney et al. | 204/414 |
| 5,338,429 A | | 8/1994 | Jolson et al. | 204/415 |
| 5,492,611 A | | 2/1996 | Sugama et al. | 204/415 |
| 5,512,882 A | * | 4/1996 | Stetter et al. | 340/632 |
| 5,601,694 A | | 2/1997 | Maley et al. | 204/415 |
| 5,605,463 A | * | 2/1997 | MacGregor et al. | 439/64 |
| 5,632,629 A | * | 5/1997 | Legrady | 439/78 |
| 5,632,875 A | | 5/1997 | Chapples et al. | 204/431 |
| 5,650,054 A | | 7/1997 | Shen et al. | 204/412 |
| 5,713,744 A | * | 2/1998 | Laub | 439/71 |

(Continued)

FOREIGN PATENT DOCUMENTS

JP 2000-009681 1/2000

(Continued)

*Primary Examiner* — Derris Banks
*Assistant Examiner* — Kaying Kue
(74) *Attorney, Agent, or Firm* — James S. Siepierski (57) ABSTRACT

This disclosure relates to an improved electrochemical sensor that has a simplified electrode assembly. The electrode assembly incorporates electrodes into or onto a single polymeric substrate. The working electrode can be porous, to enable an analyte, such as a toxic gas, to access an electrode-electrolyte interface. Ionic connection between electrodes can be made by an electrolyte on a back side of the electrode assembly, and external electronic circuitry can be connected directly to the electrode assembly. This construction dramatically simplifies the sensor, resulting in reduced costs and potentially improved performance. The construction is compatible with batch fabrication methods.

5 Claims, 8 Drawing Sheets

U.S. PATENT DOCUMENTS

| | | | |
|---|---|---|---|
| 5,761,952 A | 6/1998 | Gilby et al. | 73/1.06 |
| 5,816,827 A * | 10/1998 | Nelson et al. | 439/64 |
| 5,819,400 A * | 10/1998 | Sargeant | 29/825 |
| 5,827,948 A | 10/1998 | Martell et al. | 73/31.06 |
| 5,906,718 A | 5/1999 | Hance et al. | 204/412 |
| 5,914,019 A | 6/1999 | Dodgson et al. | 204/415 |
| 5,936,818 A * | 8/1999 | Maue et al. | 361/93.1 |
| 6,200,443 B1 | 3/2001 | Shen et al. | 204/401 |
| 6,238,799 B1 | 5/2001 | Opolski | 428/423.1 |
| 6,265,750 B1 | 7/2001 | Feng et al. | 257/414 |
| 6,454,923 B1 * | 9/2002 | Dodgson et al. | 204/415 |
| 6,666,963 B1 | 12/2003 | Peng et al. | 204/432 |
| 6,673,644 B2 | 1/2004 | Gole et al. | 438/49 |
| 6,775,125 B2 * | 8/2004 | Kimura et al. | 361/523 |
| 6,840,084 B2 | 1/2005 | Nikolskaya | 73/23.2 |
| 6,866,936 B2 | 3/2005 | Opolski | 428/413 |
| 6,872,290 B2 | 3/2005 | Dalmia et al. | 204/409 |
| 6,908,537 B2 | 6/2005 | Dalmia et al. | 204/424 |
| 6,948,352 B2 | 9/2005 | Rabbett et al. | 73/1.04 |
| 7,063,698 B2 * | 6/2006 | Whayne et al. | 606/49 |
| 7,320,616 B1 * | 1/2008 | Legrady et al. | 439/404 |
| 2002/0029613 A1 | 3/2002 | Stetter et al. | 73/31.05 |
| 2003/0024814 A1 | 2/2003 | Stetter | 204/426 |
| 2003/0233091 A1 * | 12/2003 | Whayne et al. | 606/49 |
| 2004/0090735 A1 * | 5/2004 | Kimura et al. | 361/502 |
| 2004/0214374 A1 * | 10/2004 | Sakamoto et al. | 438/113 |
| 2005/0178186 A1 * | 8/2005 | Gollar et al. | 73/31.05 |
| 2006/0185979 A1 * | 8/2006 | Suda et al. | 204/431 |
| 2006/0206113 A1 * | 9/2006 | Whayne et al. | 606/49 |

FOREIGN PATENT DOCUMENTS

| | | |
|---|---|---|
| JP | 2003-107051 | 4/2003 |
| JP | 2003-107052 | 4/2003 |
| WO | WO2005080957 * | 9/2005 |

* cited by examiner

METHODS OF MAKING AN ELECTROCHEMICAL GAS SENSOR

TECHNICAL FIELD

This disclosure relates to sensors and to methods of making the same.

BACKGROUND

Many commercially available electrochemical sensors are of the amperometric type, in which two or more electrically conductive electrodes are connected to an external circuit and communicate through an ion conductive material, called an electrolyte. When a detectable species is present, a current proportional to the species concentration is produced in the external circuit due to a REDOX reaction at the electrode surfaces. The electrodes in these sensors typically include a powder-based conductive material, which may include a catalyst such as platinum, supported by a gas permeable membrane, such as a TEFLON® film. Two or more such electrodes are then assembled in a 2D or 3D configuration within a housing and are separated from each other by an electrolyte. The electrolyte may be a liquid based electrolyte, such as an aqueous salt or acid, a gel, or solid based electrolyte, such as YSZ ceramic or a solid polymer electrolyte.

In operation, the electroactive species to be detected diffuses through the gas permeable membrane and makes contact with a first electrode, called the working electrode, where it undergoes an oxidation or reduction half reaction. Examples of half reactions on a working electrode include the following.

Carbon Monoxide Oxidation: $CO+H_2O \rightarrow CO_2+2H^{+}+2e^{-}$

Hydrogen Sulfide Oxidation: $H_2S+4H_2O \rightarrow H_2SO_4+8H^{+}+8e^{-}$

Nitrogen Dioxide Reduction: $NO_2+2H^{+}+2e^{-} \rightarrow NO+H_2O$

Chlorine Reduction $Cl_2+2H^{+}+2e^{-} \rightarrow 2HCl$

Hydrazine Oxidation: $N_2H_4+4OH^{-} \rightarrow N_2+4H_2O+4e^{-}$

Produced ion products are then transported across the electrolyte to a second electrode, called the counter electrode, where a counter oxidation or reduction half reaction occurs. The counter oxidation reactions may be accomplished, e.g., by the reduction of protons with oxygen to form water. The counter reduction reactions may be accomplished, e.g., by breaking water into hydrogen ions and oxygen. A third reference electrode optionally is utilized to improve stability of the electrical output, by maintaining a fixed potential via an external circuit.

The fine catalyst powders distributed on the membrane to produce the electrodes described above can result in high electrical resistance in the electrodes due to the discontinuous nature of the powder. In addition, the often used permeable membranes, such as those made of fluoropolymers, are hydrophobic in nature, making it difficult to maintain intimate contact with the electrolyte. Both of these factors can contribute to a higher overall cell resistance, which can result in lower current output. Electrical output from the electrodes is typically accomplished by pins which protrude out of the cell body. For example, the electrodes may be connected to the pins by a current carrying wire or ribbon sandwiched into the assembly. The net result of this type of construction can be higher costs, lower part-to-part repeatability, and lower durability.

Examples of such sensors are described in U.S. Pat. Nos. 4,227,984, 5,126,035, 5,304,293, 5,338,429, 5,650,054, 5,906,718, 5,914,019, 6,200,443, 6,454,923, 6,908,357, 6,948,352, and in U.S. Published Patent Application No. 2002/0029613.

SUMMARY

Described herein are electrochemical sensors that can be used to detect the presence of various chemical and biological moieties, such as oxygen, carbon monoxide or pathogens.

In one aspect, the disclosure features electrode assemblies that include a first electrode that includes a first conductive material, such as an agglomerated conductive material, and a second electrode that includes a second conductive material, such as an agglomerated conductive material. The first and second electrodes are carried by an insulating substrate that includes a polymeric material. For example, the electrodes can be embedded in and/or carried on a top of a polymeric substrate.

Implementations may include any one or more of the following features. The first and/or second electrode(s) has (have) one or more porous regions, each having a porosity sufficient to allow a gas to pass therethrough. Each porous region includes apertures defined in the first and/or second electrode(s). The first and/or second electrode(s) is(are) formed of a single material. The first and/or second electrode(s) is(are) formed of more than a single material, such as a metal alloy. The first and/or second electrode(s) define a first layer and a second layer. The first layer includes one or more of an inert conductor material such as carbon, gold, iridium, rhodium, platinum, or silver. The second layer includes one or more conductor materials, such as copper, steel, nickel and titanium. The first and/or second electrode(s) is(are) formed of two materials and the first material surrounds the second material. The first and second agglomerated conductive materials are substantially unitary conductive materials. The first and second electrodes carried by the insulating material are embedded in the insulating material. The electrode assembly further includes a third conductive electrode that includes a third conductive material and the third electrode is also carried by the insulating substrate. The insulating material includes a thermoplastic material. The thermoplastic material is one or more of acrylonitrile-butadiene-styrene copolymer (ABS), polycarbonate (PC), polyethylene (PE), polypropylene (PP), polyphenylene sulfide (PPS), liquid crystalline polymer (LCP) and fluoropolymer. The thermoplastic material includes mineral- or glass-filled material. The insulating material has a flexural modulus, as measured using ASTM D790, of greater than about 500,000 psi, such as greater than about 750,000 psi or 900,000 psi. The insulating material includes a thermoset material, such as a mineral-filled cured epoxy resin. The electrode assembly further includes first particles having a characteristic dimension of less than about 500 nm, such as a diameter of less than about 500 nm. The electrode assembly further includes second particles having a characteristic dimension of less than about 500 nm, such as a length of less than about 500 nm. The first and/or second particles are disposed on a surface of one or more of the electrodes. The first and/or second particles include one or more of metals, ceramics and carbon nanotubes. The particles include carbon nanotubes and each carbon nanotube includes one or more walls. One or more electrodes are about 0.0005 inch to about 0.0500 inch thick. One or more of the electrodes is subtractively patterned. One or more electrodes are additively patterned, such as by electroforming, casting, or sintered powder.

In another aspect, the disclosure features electrode assemblies that include a first electrode that includes a first agglomerated conductive material, and a second electrode that includes a second agglomerated conductive material. The first and/or second electrode(s) is (are) carried by an insulating substrate.

Implementations may include any one or more of the following features. Each electrode is carried upon an outer surface of the insulating substrate. The electrode assembly further includes one or more interlayers between each electrode and the insulating material. For example, the one or more interlayers can be an adhesive. The first and/or second electrode(s) has(have) one or more porous regions, each having a porosity sufficient to allow a gas to pass therethrough. Each porous region includes apertures defined in the first and/or second electrode(s). The first and/or second electrode(s) is(are) formed of a single material. The first and/or second electrode(s) is(are) formed of more than a single material, such as a metal alloy. The first and/or second electrode(s) define a first layer and a second layer. The first layer includes one or more of an inert conductor material such as carbon, gold, iridium, rhodium, platinum, or silver. The second layer includes one or more conductor materials, such as copper, steel, nickel and titanium. The first and/or second electrode(s) is(are) formed of two materials and the first material surrounds the second material. The first and second agglomerated conductive materials are substantially unitary conductive materials. The first and second electrodes carried by the insulating material are embedded in the insulating material. The electrode assembly further includes a third conductive electrode that includes a third conductive material and the third electrode is also carried by the insulating substrate. The insulating material includes a thermoplastic material. The thermoplastic material is one or more of acrylonitrile-butadiene-styrene copolymer (ABS), polycarbonate (PC), polyethylene (PE), polypropylene (PP), polyphenylene sulfide (PPS), liquid crystalline polymer (LCP) and fluoropolymer. The thermoplastic material includes mineral- or glass-filled material. The insulating material has a flexural modulus, as measured using ASTM D790, of greater than about 500,000 psi, such as greater than about 750,000 psi or 900,000 psi. The insulating material includes a thermoset material, such as a mineral-filled cured epoxy resin. The electrode assembly further includes first particles having a characteristic dimension of less than about 500 nm, such as a diameter of less than about 500 nm. The electrode assembly further includes second particles having a characteristic dimension of less than about 500 nm, such as a length of less than about 500 nm. The first and/or second particles are disposed on a surface of one or more of the electrodes. The first and/or second particles include one or more of metals, ceramics and carbon nanotubes. The particles include carbon nanotubes and each carbon nanotube includes one or more walls. One or more electrodes are about 0.0005 inch to about 0.0500 inch thick. One or more of the electrodes is subtractively patterned. One or more electrodes are additively patterned, such as by electroforming, casting, or sintered powder.

In another aspect, the disclosure features sensors that include an electrode assembly that includes a first electrode that includes a first conductive material, such as an agglomerated material, and a second electrode that includes a second conductive material, such as an agglomerated material. An electrolyte is in chemical communication with both the first and second electrodes and the first and second electrodes are carried by an insulating substrate that includes a polymeric material. For example, the sensors can detect one or more of oxygen, ozone, carbon monoxide, hydrazine, hydrogen cyanide, hydrogen fluoride, hydrogen sulfide, halogens, e.g., chlorine or bromine, oxides of nitrogen, e.g., nitrogen dioxide and nitrogen monoxide, oxides of sulfur, e.g., sulfur dioxide, hydrocarbons, alcohols (e.g., ethanol), formaldehyde, and pathogens, such bacteria, e.g., anthrax spores, or viruses, e.g., smallpox.

Implementations may include any one or more of the following features. The sensors further include a gas-permeable member enclosing a front side of the electrode assembly, and a substantially gas impermeable member enclosing a back side of the electrode assembly. The electrolyte is disposed on the back side of the electrode assembly. The electrolyte is a solid, a liquid or a gel. Mixtures of solids, liquids and/or gels may be utilized as electrolyte. The first and/or second electrode(s) has(have) one or more porous regions, each having a porosity sufficient to allow a gas to pass therethrough. Each porous region includes apertures defined in the first and/or second electrode(s). The first and/or second electrode(s) is(are) formed of a single material. The first and/or second electrode(s) is(are) formed of more than a single material, such as a metal alloy. The first and/or second electrode(s) define a first layer and a second layer. The first layer includes one or more of carbon, gold, iridium, rhodium, platinum, or silver. The second layer includes one or more of copper, steel, nickel and titanium. The first and/or second electrode(s) is(are) formed of two materials and the first material surrounds the second material. The first and second agglomerated conductive materials are substantially unitary conductive materials. The first and second electrodes carried by the insulating material are embedded in the insulating material. The electrode assembly further includes a third conductive electrode that includes a third conductive material and the third electrode is also carried by the insulating substrate. The insulating material includes a thermoplastic material. The thermoplastic material is one or more of acrylonitrile-butadiene-styrene copolymer (ABS), polycarbonate (PC), polyethylene (PE), polypropylene (PP), polyphenylene sulfide (PPS), liquid crystalline polymer (LCP) and fluoropolymer. The thermoplastic material includes mineral- or glass-filled material. The insulating material has a flexural modulus, as measured using ASTM D790, of greater than about 500,000 psi, such as greater than about 750,000 psi or 900,000 psi. The insulating material includes a thermoset material, such as a mineral-filled cured epoxy resin. The electrode assembly further includes first particles having a characteristic dimension of less than about 500 nm, such as a diameter of less than about 500 nm. The electrode assembly further includes second particles having a characteristic dimension of less than about 500 nm, such as a length of less than about 500 nm. The first and/or second particles are disposed on a surface of one or more of the electrodes. The first and/or second particles include one or more of metals, ceramics and carbon nanotubes. The particles include carbon nanotubes and each carbon nanotube includes one or more walls. One or more electrodes are about 0.0005 inch to about 0.0500 inch thick. One or more of the electrodes is subtractively patterned. One or more electrodes are additively patterned, such as by electroforming, casting, or sintered powder.

In another aspect, the disclosure features sensors that include an electrode assembly that includes a first electrode and a second electrode. The first and second electrodes are carried by an insulating substrate that includes a polymeric material and an electrolyte is in chemical communication with both the first and second electrodes. RMS (root-meansquare) noise of an output signal of the sensor is less than about 100 ppb output equivalent for Nitrogen Dioxide. For example, the sensors can detect one or more of oxygen, carbon monoxide, hydrazine, hydrogen cyanide, hydrogen fluoride, hydrogen sulfide, alcohols, e.g., ethanol, formaldehyde, and pathogens, such bacteria, e.g., anthrax spores, or viruses, e.g., smallpox.

Implementations may include any one or more of the following features. The first electrode includes a first agglomerated conductive material and/or the second electrode includes a second agglomerated conductive material. The sensors further include a gas-permeable member enclosing a front side of the electrode assembly, and a substantially gas impermeable member enclosing a back side of the electrode assembly. The electrolyte is disposed on the back side of the electrode assembly. The electrolyte is a solid, a liquid or a gel. Mixtures of solids liquids and/or gels may be utilized as electrolyte. The first and/or second electrode(s) has(have) one or more porous regions having a porosity sufficient to allow a gas to pass therethrough. Each porous region includes apertures defined in the first and/or second electrode(s). The first and/or second electrode(s) is(are) formed of a single material. The first and/or second electrode(s) is(are) formed of more than a single material, such as a metal alloy. The first and/or second electrode(s) define a first layer and a second layer. The first layer includes one or more of gold, iridium, rhodium, platinum, or silver. The second layer includes one or more of copper, steel, nickel and titanium. The first and/or second electrode(s) is(are) formed of two materials and the first material surrounds the second material. The first and second agglomerated conductive materials are substantially unitary conductive materials. The first and second electrodes carried by the insulating material are embedded in the insulating material. The electrode assembly further includes a third conductive electrode that includes a third conductive material and the third electrode is also carried by the insulating substrate. The insulating material includes a thermoplastic material. The thermoplastic material is one or more of acrylonitrile-butadiene-styrene copolymer (ABS), polycarbonate (PC), polyethylene (PE), polypropylene (PP), polyphenylene sulfide (PPS), liquid crystalline polymer (LCP) and fluoropolymer. The thermoplastic material includes mineral- or glass-filled material. The insulating material has a flexural modulus, as measured using ASTM D790, of greater than about 500,000 psi, such as greater than about 750,000 psi or 900,000 psi. The insulating material includes a thermoset material, such as a mineral-filed cured epoxy resin. The electrode assembly further includes first particles having a characteristic dimension of less than about 500 nm, such as a diameter of less than about 500 nm. The electrode assembly further includes second particles having a characteristic dimension of less than about 500 nm, such as a length of less than about 500 nm. The first and/or second particles are disposed on a surface of one or more of the electrodes. The first and/or second particles include one or more of metals, ceramics and carbon nanotubes. The particles include carbon nanotubes and each carbon nanotube includes one or more walls. One or more electrodes are about 0.0005 inch to about 0.0500 inch thick. One or more of the electrodes is subtractively patterned. One or more electrodes are additively patterned, such as by electroforming, casting, or sintered powder.

In another aspect, the disclosure features electrochemical sensors having electrodes that are made from a patterned metal or a metal alloy.

Implementations may include one or more of the following features. One or more electrodes are porous. The sensor detects one or more toxic gases. The sensor detects oxygen or carbon monoxide. The sensor includes two or more electrodes, e.g., three, or even four electrodes. For example, the sensor may include a porous working electrode, a counter electrode and a reference electrode. One or more of the electrodes is subtractively patterned, e.g., by utilizing a mechanical or chemical process. One or more electrodes are additively patterned by an electroforming, casting, or sintered powder. One or more electrodes are about 0.0005 inch to about 0.0500 inch thick. One or more electrodes can include a catalyst coating, such as carbon, carbon nanotubes, noble metals, metal oxides, diamond, enzymes or enzyme-selective materials. For example, the catalyst may be applied by chemical or vapor deposition. For example, the catalyst can be applied by solution processing, such as electrophoresis, electroplating, or dip coating. For example, the catalyst can be applied by a spray coating or printing process. The first electrode includes a first agglomerated conductive material and/or the second electrode includes a second agglomerated conductive material. The sensors further include a gas-permeable member enclosing a front side of the electrode assembly, and a substantially gas impermeable member enclosing a back side of the electrode assembly. The electrolyte is disposed on the back side of the electrode assembly. The electrolyte is a solid, a liquid or a gel. Mixtures of solids liquids and/or gels may be utilized as electrolyte. The first and/or second electrode(s) has(have) one or more porous regions, each having a porosity sufficient to allow a gas to pass therethrough. Each porous region includes apertures defined in the first and/or second electrode(s). The first and/or second electrode(s) is(are) formed of a single material. The first and/or second electrode(s) is(are) formed of more than a single material, such as a metal alloy. The first and/or second electrode(s) define a first layer and a second layer. The first layer includes one or more of carbon, gold, iridium, rhodium, platinum, or silver. The second layer includes one or more of copper, steel, nickel and titanium. The first and/or second electrode(s) is(are) formed of two materials and the first material surrounds the second material. The first and second agglomerated conductive materials are substantially unitary conductive materials. The first and second electrodes carried by the insulating material are embedded in the insulating material. The electrode assembly further includes a third conductive electrode that includes a third conductive material and the third electrode is also carried by the insulating substrate. The insulating material includes a thermoplastic material. The thermoplastic material is one or more of acrylonitrile-butadiene-styrene copolymer (ABS), polycarbonate (PC), polyethylene (PE), polypropylene (PP), polyphenylene sulfide (PPS), liquid crystalline polymer (LCP) and fluoropolymer. The thermoplastic material includes mineral- or glass-filled material. The insulating material has a flexural modulus, as measured using ASTM D790, of greater than about 500,000 psi, such as greater than about 750,000 psi or 900,000 psi. The insulating material includes a thermoset material, such as a mineral-filled cured epoxy resin. The electrode assembly further includes first particles having a characteristic dimension of less than about 500 nm, such as a diameter of less than about 500 nm. The electrode assembly further includes second particles having a characteristic dimension of less than about 500 nm, such as a length of less than about 500 nm. The first and/or second particles are disposed on a surface of one or more of the electrodes. The first and/or second particles include one or more of metals, ceramics and carbon nanotubes. The particles include carbon nanotubes and each carbon nanotube includes one or more walls.

In another aspect, the disclosure features electrochemical sensors, e.g., of the amperometric type, that utilize enhanced electrode assemblies. The assemblies include a single substrate having two or more electrodes, e.g., a working, a counter and a reference electrode, as well as circuitry to enable external electrical connection.

Implementations may include any one or more of the following features. Porous materials are structured or attached to an electrode assembly. For example, in operation, the porous materials can be used as a replacement for powder-based materials. Powdered materials can be subsequently applied to the surface of a porous structure, or made to be in contact with the porous structures, such as by clamping, in order to further improve performance of the sensor. The substrate can be first patterned with a plurality of holes, e.g., to make the substrate porous for gas access and electrical connection between the front and back of the substrate. One or more electrodes and circuitry can be deposited and patterned onto any substrate. The substrate can be an insulating material, such as plastic, glass, ceramic, or silicon. The substrate can be patterned by chemical etching, laser ablation, or mechanical methods. Any electrode can be deposited by chemical or physical vapor deposition, lamination, screen printing, electroless or electroplating. A working electrode can be a porous conductive membrane spanning across a relatively large opening in the substrate. The working electrode can be a patterned foil, e.g., made of metal or a metal alloy, or a bonded, porous conductor, such as anodized metal, porous metal, e.g., provided through powder metallurgy, or porous carbon, such as activated carbon. The substrate can be made thin in the area of the working electrode, e.g., to allow for a greater number of holes for improved sensitivity. The electrode materials can contain one or more catalysts, such as a precious metal, e.g., platinum and/or an enzyme, applied to a surface of the porous structure. The electrodes can be first patterned, and then an insulating substrate can subsequently added, e.g., by insert molding. An insulating tape can be used to support the electrodes instead of a subsequently molded insulator. If desired, the electrode assembly can include only a working electrode and counter electrode (i.e., no reference electrode is employed). Alternatively, a working, a counter, and a reference electrode can be utilized in the assembly. Additional electrodes, e.g., working electrodes, can be incorporated so that there are a total of 4, 5, 6 or even more electrodes. Multiple working electrodes can be utilized to detect multiple analytes. A housing can be utilized to house an electrolyte and the electrode assembly. For example, the electrolyte can be a liquid, a gel or a solid.

In another aspect, the disclosure features methods of making electrode assemblies that include selecting a pre-form that includes a conductive material, such as an agglomerated conductive material, the pre-form including a plurality of device regions spaced apart in a first direction and spanning the pre-form in a second direction, each device region comprising two or more pre-electrode regions spaced apart in the first direction and extending across the pre-form in the second direction. The two or more pre-electrode regions are in electrical communication. An insulating material that includes a polymeric material is formed about each device region in a manner that the insulating material fills a spacing defined in the first direction between the two or more pre-electrode regions to provide an assembly.

Implementations may include one or more of the following features. The methods further include severing electrical communication between the two or more pre-electrode regions to provide an electrode assembly. Each device region includes three pre-electrode regions and one or more electrode regions include one or more porous regions. Each porous region includes a plurality of apertures. The forming of the insulating material about each device region is performed using injection molding. The pre-form is made by stamping or etching a sheet of metal. The pre-form is made by electroforming. The pre-form has a width of from about 0.25 inch to about 3 inches. The preform has a length of greater than 1 foot, such as greater than about 25 feet or even greater than 100 feet. The preform has a maximum thickness of from about 0.001 inch to about 0.1 inch. The conductive material has a mass density of greater about 75 percent theoretical or maximum density. The conductive material has a porosity of less than about 25 percent.

In another aspect, the disclosure features methods of making electrode assemblies that include selecting a pre-form that includes a conductive material, such as an agglomerated conductive material, and having two or more spaced apart pre-electrodes in electrical communication; forming an insulating material that includes a polymeric material about the pre-form in a manner that the insulating material fills a spacing defined between the pre-electrodes to provide an assembly; and severing electrical connection to provide discrete and spaced apart electrodes carried by the insulating material.

Implementations may include one or more of the following features. The forming of the insulating material about each device region is performed using injection molding. The pre-form is made by stamping a sheet of metal. The preform is made by electroforming. The preform has a width of from about 0.25 inch to about 3 inches. The preform has a length of greater than 1 foot, such as greater than about 25 feet or even greater than 100 feet. The preform has a maximum thickness of from about 0.001 inch to about 0.1 inch. The conductive material has a mass density of greater about 75 percent theoretical or maximum density. The conductive material has a porosity of less than about 25 percent.

In another aspect, the disclosure features methods of making electrode assemblies that include selecting a self-supporting pre-form including an agglomerated conductive material; forming a plurality of apertures in the self-supporting pre-form to provide a porous electrode; and bonding the porous electrode onto an insulating substrate.

Implementations may include any one or more of the following features. The methods further include bonding one or more additional electrodes onto the insulating substrate, such as one that includes silicon. Apertures are formed by etching. The methods further include forming one or more apertures in the insulating substrate under the porous electrode in a manner to allow a gas to pass through the porous electrode and the insulating material.

In another aspect, the disclosure features methods of making gas or vapor sensors that include providing an insulating substrate and forming one or more electrodes on the insulating substrate, such as a polymeric or silicon-containing substrate. Each electrode includes an agglomerated conductive material.

Implementations may include any one or more of the following features. Each electrode is formed by electroplating. Each electrode is formed by physical or chemical vapor deposition. Each electrode is formed by screen printing. More than a single electrode is formed on the insulating material, such as two, three, four or even five electrodes. Each electrode is discrete and spaced apart. Three electrodes are formed. One or more electrodes define a plurality of apertures. The insulating substrate defines a plurality of apertures.

Aspects or implementations of the disclosure can include one or more of the following advantages. Greatly simplified electrochemical sensors can be provided with reduced cost.

Sensors can be more stable and the electrode assemblies can have a lower overall resistivity and lower RMS noise for greater sensitivity.

An electrically insulating material is one having a resistivity of greater than about $1\times10^7$ ohm·cm at 25° C., e.g., between about $1\times10^{10}$ to about $1\times10^{15}$ ohm·cm at 25° C.

A polymeric material is one that has distinguishable repeat units and includes carbon and hydrogen atoms along a backbone and/or extending from a backbone. Optionally, the backbone and/or pendent groups can also include other elements, such as C, S, Si, or P. For example, a polymeric material can include a polyolefin, a polyamide, a polyimide, a polysiloxane or a cured epoxy resin. The polymeric material can be cross-linked or thermoplastic in nature.

Porosity can be measured using mercury porosimetry.

A non-porous material is one having less than five percent porosity, as measured using mercury porisimetry, while a porous material is one having a porosity of greater than or equal to five percent.

All publications, patent applications, patents, and other references mentioned herein are incorporated by reference herein in their entirety for all that they contain. In case of conflict, the present specification, including definitions, will control. In addition, the materials, methods, and examples are illustrative only and not intended to be limiting.

Other features and advantages of the disclosure will be apparent from the following detailed description, and from the claims.

DETAILED DESCRIPTION

This disclosure relates to an improved electrochemical sensor that has a simplified electrode assembly. The electrode assembly incorporates electrodes into or onto a polymeric substrate. The working electrode can be made porous, to enable an analyte, such as a toxic gas, to access an electrode-electrolyte interface. Ionic connection between electrodes can be made by an electrolyte on a back side of the electrode assembly, and external electronic circuitry is connected directly to the electrode assembly. This construction dramatically simplifies the sensor, eliminating need for current collectors, pins, gas permeable membranes, electrode powders, and complex housings. The construction is compatible with batch fabrication methods.

Referring to FIGS. 1A-4C, a gas sensor 10 includes an electrode assembly 12 that defines a cavity or pocket 14 for holding electrolyte 16, here illustrated as a clear material so that details of the electrode assembly can be seen. Electrode assembly 12 includes a working electrode 18 that includes a porous region 20 that defines a plurality of pores or apertures 22, a reference electrode 26 and a counter electrode 30. Each electrode 18, 26 and 30 includes or is formed of an agglomerated conductive material, e.g., a porous or a non-porous material (unitary material). Each conductive material used to fashion each electrode can be the same material or each can be fashioned from a different material. As shown, each electrode is embedded by an insulating material 21 that includes a polymeric material, such as a glass or mineral-filled thermoplastic. The insulating material defines a front cavity or pocket 40 and the working electrode 18 is disposed at the bottom of the pocket 40. The front side of the electrode assembly is protected by a gas permeable membrane, such as one fashioned out of a fluoropolymer. Membrane 42 allows gases to pass into the device for easy detection, while keeping out liquids, such as water, that could damage the device. The backside of the device that includes the electrolyte in chemical communication with each electrode is closed with a gas impermeable cover 50, such as one formed of a polymeric material. The cap can be fixed in place, e.g., using an adhesive, solvent bonding, heat staking, laser welding, press fitting or ultrasonic welding. When assembled, the device 10 communicates with electronic circuitry via electrical connections 60 that are accessible on the front side of the device.

Figure 1A:
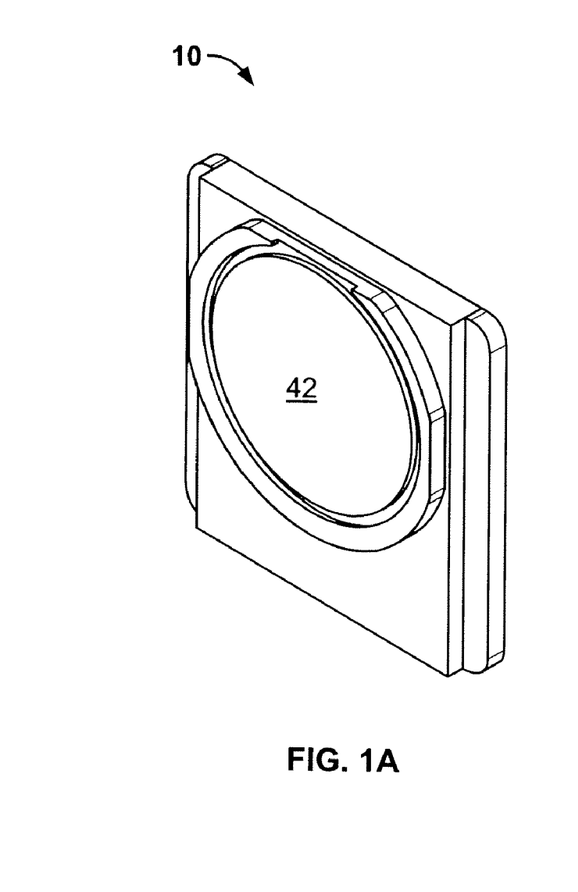
FIG. 1A is a perspective front view of a sensor, showing an analyte permeable membrane side.
Figure 1B:
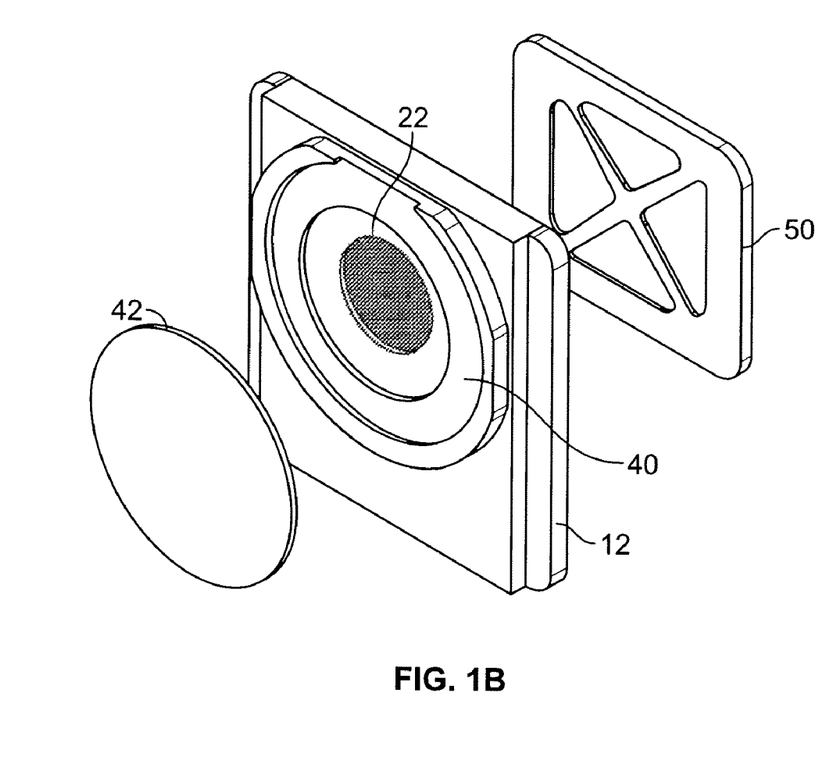
FIG. 1B is an exploded front side perspective view of the sensor shown in FIG. 1A, illustrating an analyte permeable membrane, an electrode assembly and an electrolyte cover.
Figure 2A:
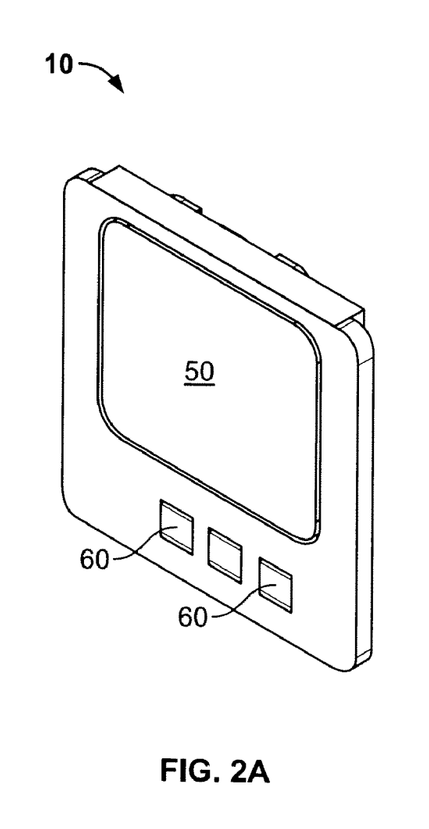
FIG. 2A is a perspective rear view of a sensor, showing an analyte impermeable cover side.
Figure 2B:
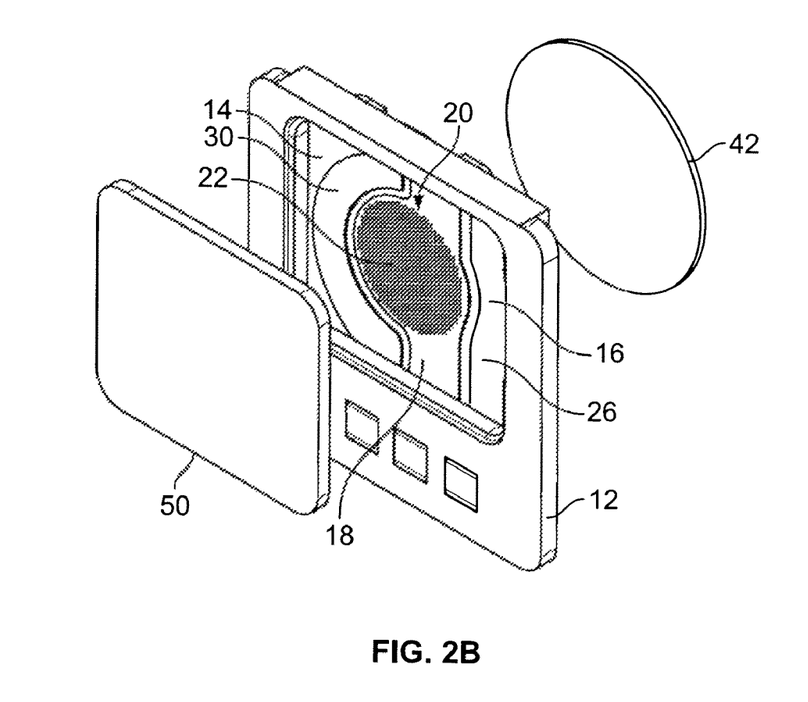
FIG. 2B is an exploded rear side perspective view of the sensor shown in FIG. 2A, illustrating an analyte impermeable cover, an electrode assembly and an analyte permeable membrane.
Figures 3, 3A, 3B:
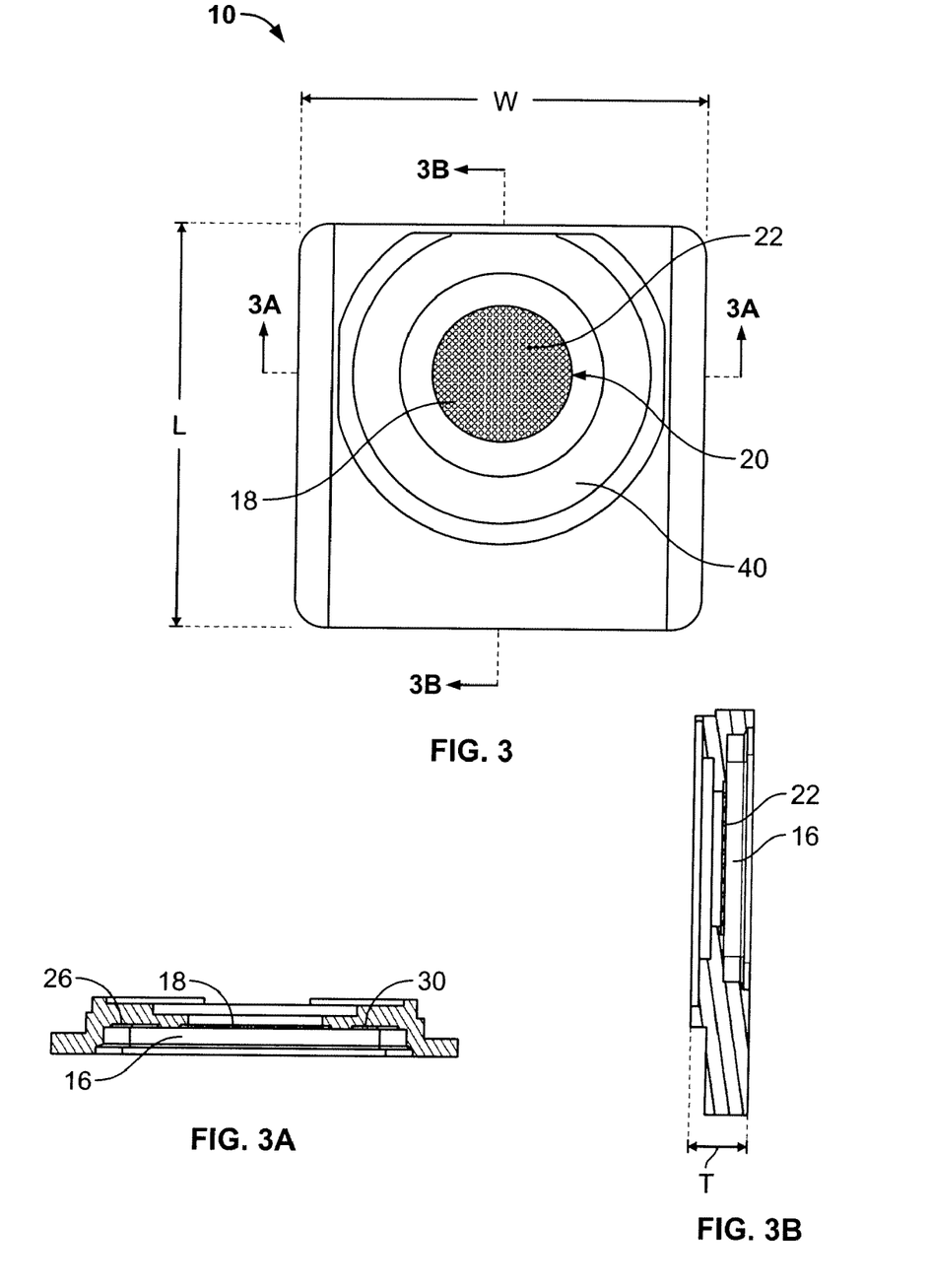
FIG. 3 is a top view of the electrode assembly shown in FIG. 1B.
FIGS. 3A and 3B are cross-sectional view of the electrode assembly of FIG. 3, taken along lines 3A-3A and 3B-3B, respectively.
Figure 4A:
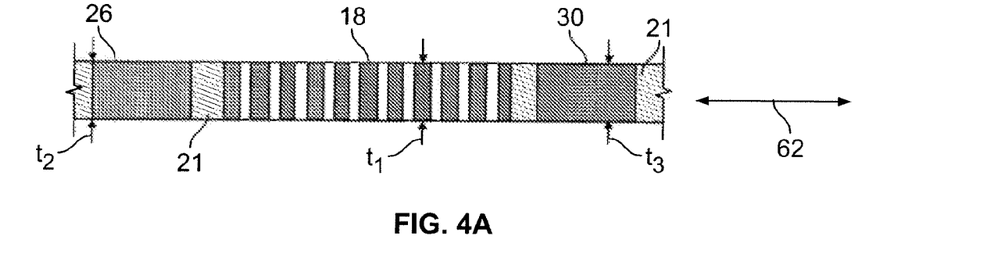
FIG. 4A is an enlarged cross-sectional view of a portion of the electrode assembly shown in FIG. 3, taken along line 3A-3A, highlighting the region about the electrodes.
Figure 4B:
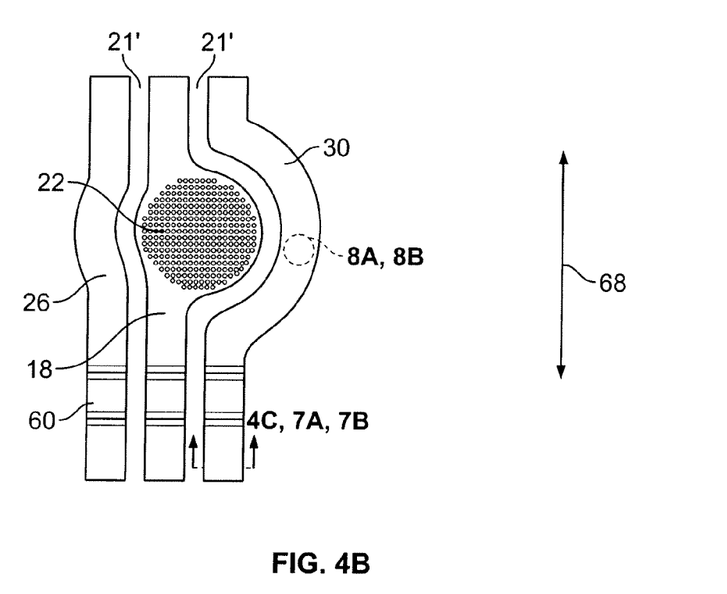
FIG. 4B is a top view of the electrode assembly of FIG. 3, with insulating material removed.

Referring particularly to FIGS. 4A and 4B, each discrete electrode does not directly touch another electrode, but is spaced apart from other electrodes in a first direction, as indicated by double arrow 62. Each electrode also extends in a second direction along the electrode assembly 10 in a direction generally perpendicular to the first direction, as indicated by double arrow 68. Insulating material 21 fills first direction spacing 21' between each electrode.

These simplified electrochemical sensors can be provided at a reduced cost with lower background noise and higher sensitivity. While not wishing to be bound by any particular theory, it is believed that the new sensor accomplishes this improvement in performance, at least in part, because the solid, continuous (aggregated) metal electrodes are more mechanically stable and of lower electrical resistance in comparison to the powder-based electrodes currently standard in the industry. For example, the electrodes described herein may have an electrical resistance of less than 10 ohms, whereas a purely powder based electrode may have an electrical resistance of greater than 1,000 ohms.

The sensors can be constructed to detect one or more of oxygen, ozone, carbon monoxide, hydrazine, hydrogen cyanide, hydrogen fluoride, hydrogen sulfide, halogens, e.g., chlorine or bromine, oxides of nitrogen, e.g., nitrogen dioxide and nitrogen monoxide, oxides of sulfur, e.g., sulfur dioxide, hydrocarbons, formaldehyde, and alcohols, e.g., ethanol. In some implementations, the sensors can detect bacteria, e.g., anthrax spores, or viruses, e.g., smallpox.

Sensors constructed in such a fashion can be small. For example, and by particular reference to FIGS. 3 and 3B, a width (W) and/or a length (L) of any sensor described herein can be from about 0.2 inch to about 1.5 inches, e.g., between about 0.25 inch to about 1.25 inches or between about 0.5 inch and about 1.0 inch. For example, a maximum thickness for any sensor can be between about 0.05 inch to about 0.5 inch, e.g., between about 0.075 inch and about 0.35 inch or between about 0.10 inch and about 0.25 inch.

Electrodes 18, 26 and 30 can be thin. For example and by reference particularly to FIG. 4A, working electrode 18, reference electrode 26 and counter electrode 30 can each have an thickness ($t_1$), ($t_2$) and ($t_3$), respectively, e.g., of from about 0.0005 inch to about 0.07 inch, e.g., from between about 0.005 inch to about 0.05 inch or from about 0.007 to about 0.025 inch. As shown in FIG. 4A, each electrode can have substantially the same thickness.

Solid, liquid, e.g., strong acids or bases, or gel electrolytes can be utilized in the sensors. An example of a solid electrolyte is yttria-doped zirconia. In addition, mixtures of solids, liquids and gels may be utilized. For example, the electrolyte can be a liquid/solid hybrid, a liquid/gel hybrid, a gel/solid hybrid or a gel/solid/liquid hybrid.

Pores 22 can define a circular shape, or a non-circular shape. For example, when they define a circular shape, they can have a diameter of between about 0.001 inch and about 0.1 inch, e.g., between about 0.001 and about 0.02 inch, or between about 0.0015 inch and about 0.01 inch.

Figure 4C:
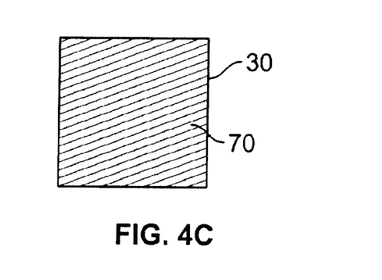
FIG. 4C is a cross-sectional view of an electrode shown in FIG. 4B, taken along line 4C-4C.

Referring particularly now to FIG. 4C, in some implementations, one or more of the electrodes is formed of a single material, such as a metal or a metal alloy, that is arranged in a single layer 70. In specific implementations, the cross-sectional view of each electrode of the assembly is the same as that exemplified for electrode 30 in FIG. 4C. In some implementations, each electrode is formed of a different material, but the material of each electrode is arranged in a single layer. In some implementations, each electrode is formed of more than a single material arranged in more than a single location along the electrode.

Each electrode or each portion of an electrode can be formed of or include carbon, gold, iridium, rhodium, platinum, silver, copper, steel, nickel, titanium or mixtures of these.

The construction of the electrodes will depend upon the material to be detected. For example, if carbon monoxide is to be detected, platinum is preferred because it can serve as an oxidation catalyst for carbon monoxide.

In some implementations, one or more electrodes is formed of a porous material, e.g., having a porosity of between about 5 percent and about 75 percent, e.g., between about 7.5 percent and about 60 percent, between about 8.0 percent and about 50 percent or between about 10 percent and 40 percent. Enhancing the porosity of the material from which the electrodes are formed can enhance surface area and, thus, reaction rates and sensitivity.

In some implementation, each electrode is formed of a material that has a density of less than 95 percent of its maximum density, e.g., between about 90 percent and 50 percent, between about 85 percent and about 60 percent or between about 80 percent and about 65 percent of its theoretical density.

In some embodiments, one or more of the agglomerated conductive materials can define substantially unitary conductive materials, such as having less than 5 percent porosity, e.g., less than 2.5 percent or less than 1 percent porosity and approaching 100 percent theoretical or maximum density of the material.

The insulating material can be thermoplastic or a thermoset material. For example, the thermoplastic material can be acrylonitrile-butadiene-styrene copolymer (ABS), polycarbonate (PC), polyethylene (PE), polypropylene (PP), polyphenylene sulfide (PPS), liquid crystalline polymer (LCP), fluoropolymer. Melt blends of such polymers can also be utilized. Examples of thermosets include, e.g., epoxy resin, polyurethane and melamine resin.

Any polymeric material described herein can include a filler material such as glass or mineral filler, e.g., to increase the rigidity or insulating properties of the material. Enhancing rigidity can protect the sensor or components of the sensor from bending and failure.

For example, the insulating material can have flexural modulus, as measured using ASTM D790, of greater than about 500,000 psi, greater than 600,000 psi, greater than 700,000 psi, greater than 800,000 psi, greater than 900,000 psi, greater than 1,000,000 psi or even greater than 1,100,000 psi.

Generally, in one method of making an electrode assembly, a pre-form is selected that includes a conductive material and that has two or more spaced apart pre-electrodes in electrical communication. An insulating material that includes a polymeric material is formed about the pre-form in a manner that the insulating material fills a spacing defined between the pre-electrodes to provide a pre-electrode assembly. Finally, the electrical connection between the two or more spaced apart pre-electrodes is severed to provide discrete and spaced apart electrodes carried by the insulating material.

Figure 5A:
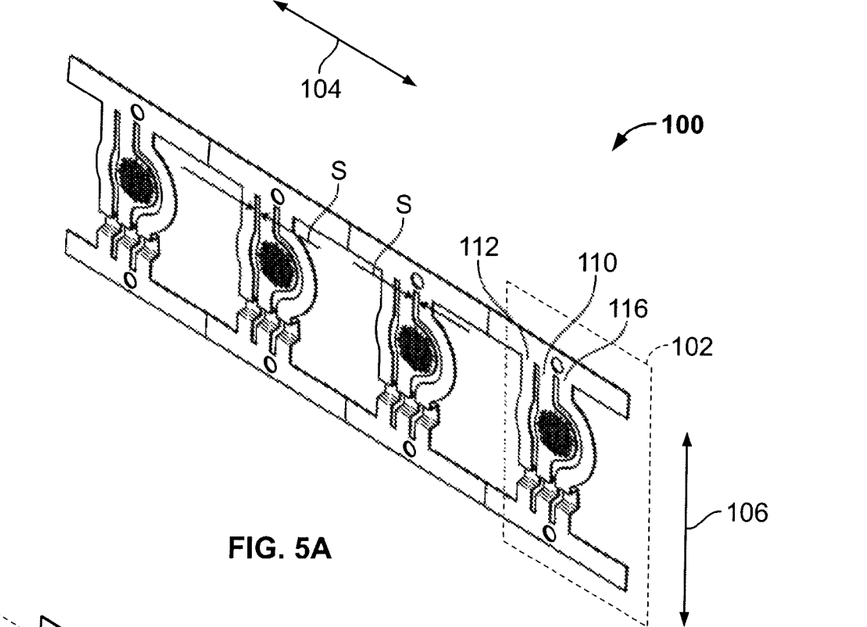
FIG. 5A is a perspective view of a pre-form.
Figure 5B:
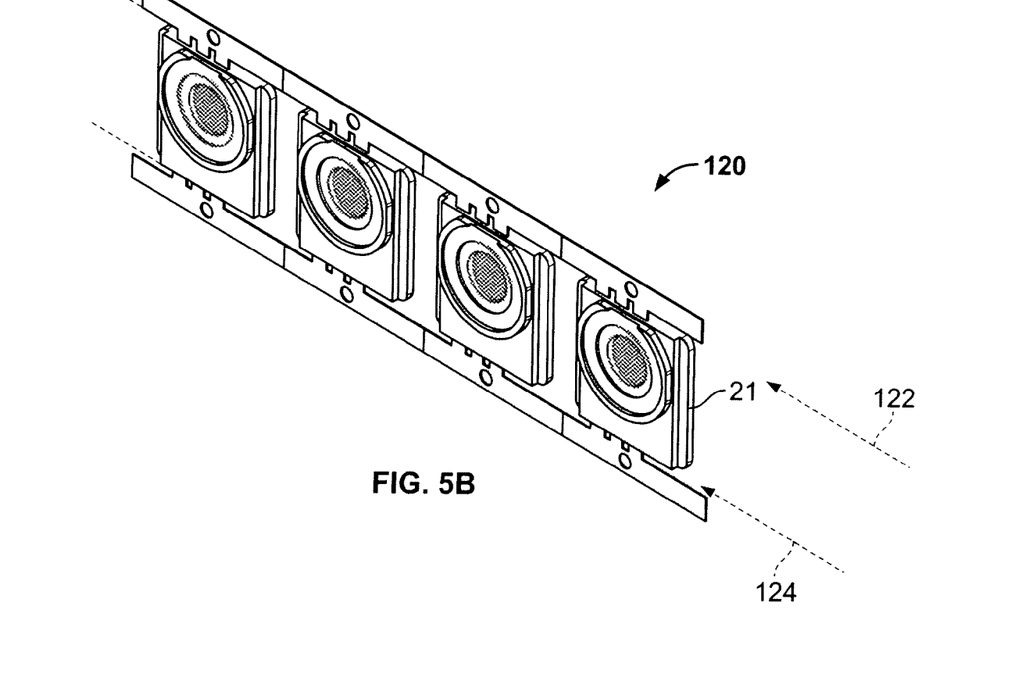
FIG. 5B is a perspective view of the pre-form shown in FIG. 5A with insulating material molded about device regions.

Referring to FIGS. 5A and 5B, one method of making electrode assembly 12 (see FIGS. 1A and 1B) starts by selecting a pre-form 100 that includes any agglomerated conductive materials described herein. The pre-form includes a plurality of device regions 102 spaced apart in a longitudinal direction, as indicated by double arrow 104, and spanning the pre-form in a lateral direction perpendicular to the longitudinal direction, as indicated by double arrow 106. Each device region includes three pre-electrode regions (in this particular instance), 110, 112, and 116, respectively, that will become the working, reference and counter electrodes of the device, spaced apart in direction 104 and extending across the pre-form in the second direction 106. As can be seen from FIG. 5A, the electrode regions are in electrical communication with one another. Next, an insulating material 21 that includes a polymeric material is formed about each device region 102 in a manner that the insulating material fills a spacing (S) defined in the first direction between the electrodes to provide a pre-electrode assembly 120. To release the individual devices, electrical communication between each electrode is severed by cutting the pre-form along lines 122 and 124.

In some implementations, the forming of the insulating material about each device region is performed using injection molding, e.g., by inserting the pre-form in an insert mold and using any of the thermoplastic materials described herein.

In other implementations, the insulating material is formed about each device by casting, e.g., using any polymeric material described herein.

For example, the pre-form can be made by using an additive process, e.g., by stamping a sheet of metal, electroforming, casting or powder sintering. In other implementations, the pre-form can be made using a subtractive process, e.g., chemical or mechanical etching.

In some implementations, the pre-form has a lateral dimension (in direction 106) of from about 0.25 inch to about 3 inches, e.g., from about 0.35 inch to about 1.5 inches or between about 0.5 inch to about 1.25 inches. In some implementations, the pre-form has a longitudinal length (in direction 104) that is between about 1 foot and about 300 feet, e.g., between about 5 feet and about 100 feet. In some implementations, pre-form 100 forms part of a continuous length from a spool, e.g., that includes more than 500 feet, or more than even 1,500 feet. In some implementations, the pre-form has a maximum thickness of from about 0.001 inch to about 0.3 inch, e.g., from about 0.001 inch about 0.1 inch.

EXAMPLES

Figure 6:
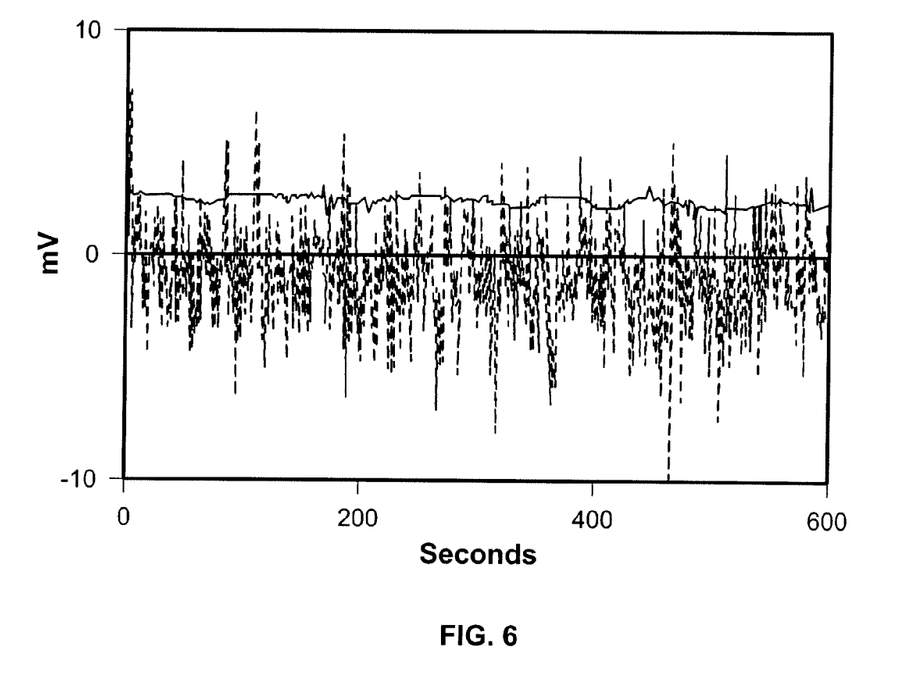
FIG. 6 is a graph of sensor response (in mV) versus time (in seconds).

FIG. 6 shows sample baseline data of different sensors. Sensors of the type described herein were comparatively tested against existing industry standard sensors of the type described in the Background Section. Each of the sensors was attached to a potentiostat circuit with a 0V bias between the reference and working electrode. The sensors were then exposed to nitrogen dioxide ($NO_2$) gas at 5 ppm (balance air), and their output from the potentiostat was adjusted to give a response of about 32 mV/ppm $NO_2$. While yielding an essentially equivalent response in magnitude, the baseline noise at 0 ppm was substantially different, as shown in FIG. 6. In this graph, the solid plot (above the zero line) is of the sensor described herein, while the dashed plot is of the industry standard sensor. From the graph, the root-mean-square (RMS) value was calculated for the black plot to be 0.2 mV, while the gray line was 2.3 mV. This indicates that the sensor described herein has <1/10 the baseline noise as the industry standard device. Noise is important when determining sensor resolution and sensitivity. While not wishing to be bound by any particular theory, it is believed that the sensor described herein accomplishes this improvement in performance, at least in part, because of the stability of the design described herein. The solid, continuous (aggregated) metal electrodes of the sensors described herein are more mechanically stable and of lower resistance in comparison to the powder-based electrodes currently standard in the industry.

Other Implementations

A number of implementations have been described. Nevertheless, it will be understood that various modifications may be made without departing from the spirit and scope of the disclosure.

For example, electrodes described herein may be coated with hydrophilic material to enhance interaction between electrolyte and electrode. For example, the coating can be or can include polyacrylic acid, polyethylene glycol, polyvinylpyrrolidone, polyacrylamide, polyvinyl alcohol, polyvinyl ethers and mixtures and salts thereof. Suitable hydrophilic coatings are those describe in Opolski, U.S. Pat. Nos. 6,238,799 and 6,866,936. The coatings can be crosslinked.

While sensors have been shown that utilize three electrodes, in some implementations, sensor use two electrodes, or four, five or even six electrodes.

While electrode assemblies have been shown in which only the working electrode has a porous region, in some implementations, other electrodes, such as the reference and counter electrodes also have porous regions.

While implementations have been shown that include electrodes that have a single porous region, in some implementations, one or more electrodes have one or more porous regions.

Figure 7A:
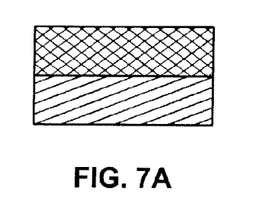
FIG. 7A is a cross-sectional view of an electrode having a layer structure, taken along the line 7A-7A of FIG. 4B.
Figure 7B:
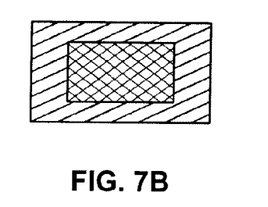
FIG. 7B is a cross-sectional view of an electrode in which a first material is encapsulated by a second material, taken along the line 7B-7B of FIG. 4B.

While electrodes have been shown that have a single layer of material, in some implementations, the electrodes have more than one layer of material. For example, each electrode can have two, three, four or even five layers. For example, a sensor can include three electrodes and the first electrode can have a single layer, the second layer can have two layers (see FIG. 7A) and the third layer can have three layers. The material of each layer can be the same or different. In other implementations, electrodes are provided in which one material encapsulates another material (see FIG. 7B). For example, a non-noble metal can be coated by a noble metal. For example, the noble metal can serve as a catalyst. One metal can be layered on another metal by chemical or physical deposition, solution deposition, such as electrophoresis, electroplating, dip or spray coating or even screen printing.

Figure 8A:
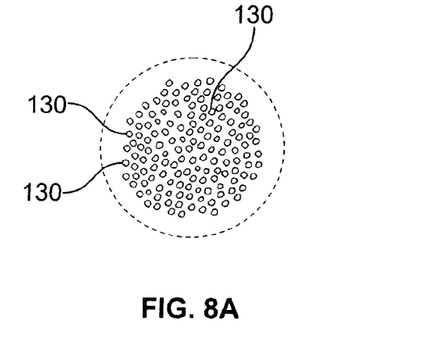
FIGS. 8A and 8B are highly enlarged schematic top views of a portion of an electrode having first particles (FIG. 8A) and first and second particles (FIG. 8B), taken in the region denoted by the line 8A, 8B in FIG. 4B.
Figure 8B:
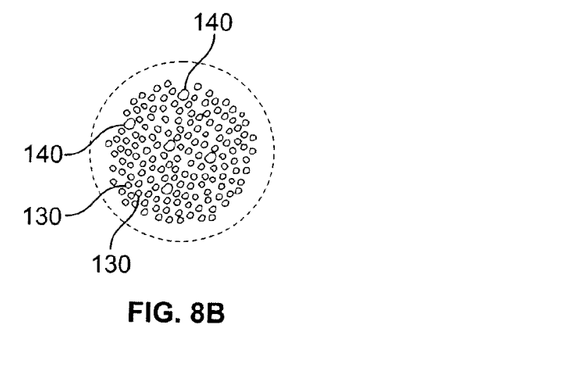

By reference to FIGS. 4B, 8A and 8B, any electrode assembly described herein can include first particles 130 having a characteristic dimension of less than about 500 nm, such as a diameter of less than about 500 nm (FIG. 8A). In other implementations, any electrode assembly described herein can include first particles 130 and second particles 140, each having a characteristic dimension of less than about 500 nm, such as a length of less than about 500 nm. For example, the first and/or second particles can disposed on a surface of one or more of the electrodes (see FIG. 4B). For example, the first and/or second particles can include one or more metals, one or more ceramics, one or more carbon nanotubes, such as one having a single or a double wall. Mixtures of these particles can also be utilized. For example, the particles can serve as a catalyst and can be deposited on a surface by spray coating, screen printing, or by compressing onto the electrode surface before or during the assembly of the sensor. Other materials may be deposited on a surface of the any electrode, such as enzymes.

While implementations have been described in which electrodes are embedded in an insulating material, in some implementations, one or more electrodes are carried upon an outer surface of an insulating material. In some implementations, all electrodes of an electrode assembly are carried upon an outer surface of an insulating material.

While implementations have been shown in which the insulating material is or includes a polymeric material, in some implementations, the insulating material is or includes other materials, such as ceramics and silicon. For example, in specific implementations, the insulator includes silicon dioxide or silicon encapsulated by silicon dioxide.

Figure 9:
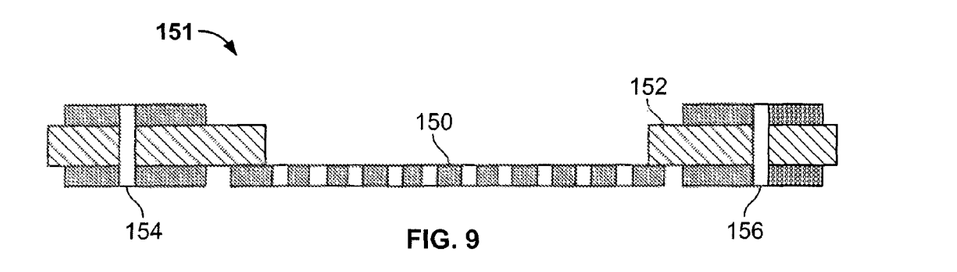
FIGS. 9-11 are cross-sectional views of alternative electrode assemblies.

Referring now to FIG. 9, in one alternative implementation, a working electrode 150 is a self supporting porous membrane. For example, making such a membrane can be achieved by using a base metal, such as a foil, and patterning a porous structure, such as by etching or pattern electroplating. Alternatively, the working electrode could be a selected porous structure, such as a structure made of porous metal, porous carbon, or porous silicon. In either case, the provided working electrode can be subsequently bonded to a substrate 152. If desired, a surface catalyst can be incorporated into any electrode by any of the methods described herein. A counter 154 and a reference electrode 156 can be utilized, which can be made by any method described herein. The substrate can then be opened in the region 151 above the working electrode, such as by using chemical etching.

Figure 10:
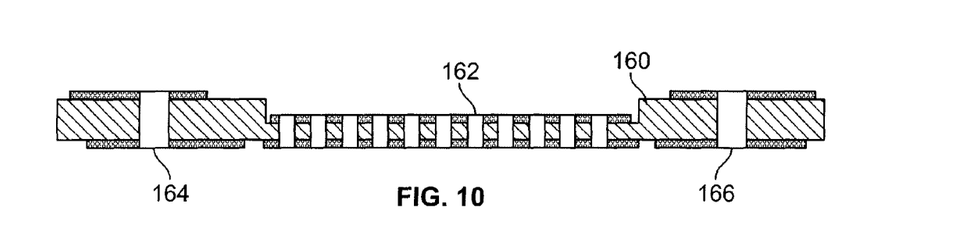

Referring to FIG. 10, in another alternative implementation, an insulating substrate 160 is made thin in a region about a working electrode 162. For example, the thinned region can be made either by starting with a substrate of the desired shape (e.g., molded in the desired shape), or by removing material from a pre-form by physical or chemical methods. The remainder of the electrode assembly, including fabrication of a counter 164 and reference electrode 166, can be made by any of the methods described herein. For example, the thinned region can enable smaller holes for the working electrode 162, since the size of the holes is determined by the process used and the material thickness, which will govern a maximum aspect ratio. For example, if a standard isotropic wet etching process is utilized, the thickness to hole diameter aspect ratio is generally limited to 1:1. The thinner region allows for smaller diameter holes, enabling a greater number of total holes, which can increase the total hole perimeter length at the electrolyte interface, which, in turn, can increase current output.

Figure 11:
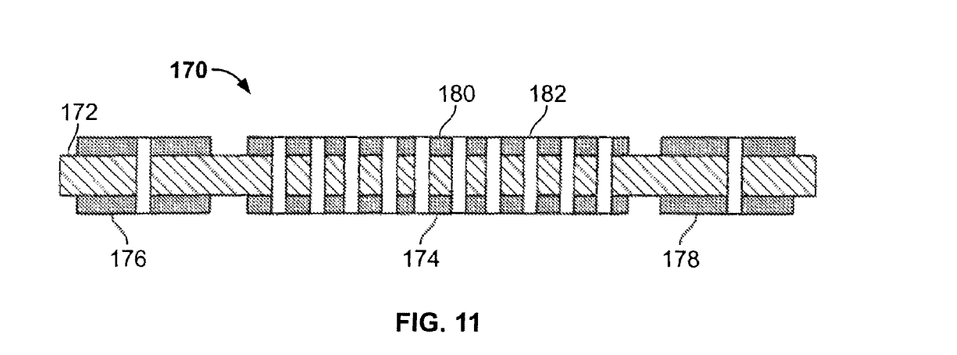

Referring to FIG. 11, in yet another alternative implementation, an insulating substrate 172 is used to support a set of electrodes for the detection of a particular gas of interest. In the implementation shown, the electrode assembly 170 has a working electrode 174, a counter electrode 176 and a reference electrode 178. For example, the substrate 172, which can be made of silicon, ceramic, or plastic, is made porous by forming a plurality of holes 182 through the substrate. For example, the holes can be made by laser ablation, chemical etching or punching. In the specific case of silicon, which may be conductive, a follow on insulating layer of silicon dioxide or other material can applied over the entire substrate by thermal oxidation, CVD or PVD. The substrate may be as thin as 1 micron, and as thick as 10 mm, and the diameters of the holes may be as small as 10 nanometers, and as large as 10 mm. The preferred porous structure includes several holes in the region of the working electrode and only 1 or 2 holes in the region of the counter and reference electrodes. Once the substrate has been made porous, the electrodes and topside circuitry 180 may be deposited. These features may be patterned by standard methods, such as lithography or stenciling. The materials used for the circuit may be of any conductive material, and may include at the surface, a catalyst material such as gold, platinum, rhodium, palladium or silver. Enzyme based catalysts may also be applied to the surface for specific applications, such as biological detection (e.g., glucose oxidase for glucose monitoring). Preferred methods of applying the electrodes and circuit in such implementations, include physical and chemical vapor deposition, electroless and electrolytic plating, dip coating and screen printing. In operation, the bottom side of the substrate is in contact with an electrolyte (not shown) and the top side circuit pattern is exposed to the environment. Electrical connection between the two sides can be made during the patterning process of the conductors. The thickness of the conductor can be adjusted so that it does not significantly fill the holes of the working electrode; otherwise an analyte can be prevented from freely traveling through the porous substrate to interface between the working electrode and the electrolyte. The holes connecting the counter and reference electrodes are preferably filled for improved performance. However, in some embodiments, the holes are not filled.

Figure 12:
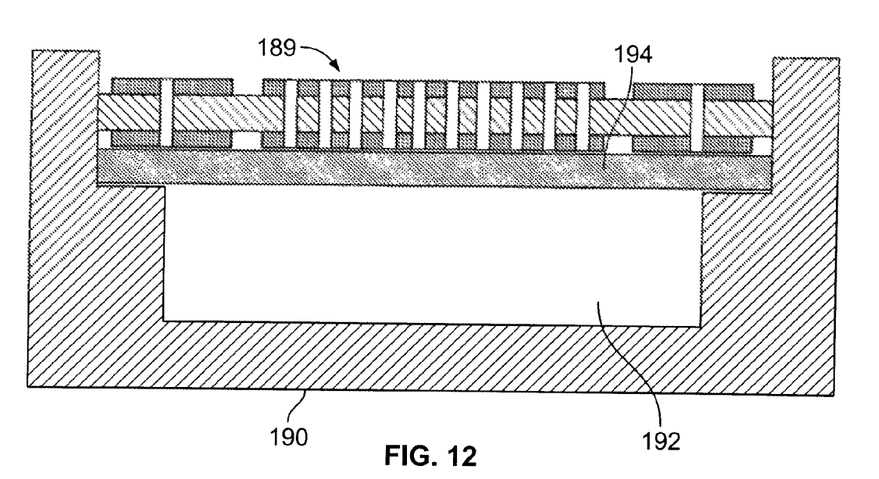
FIGS. 12 and 13 are cross-sectional views of alternative sensors.

Referring now to FIG. 12, in an alternative sensor design, an electrode assembly 189 is mounted in a housing 190, which defines an electrolyte reservoir 192. The housing maintains the electrode assembly in intimate contact with an electrolyte, which could be in the form of liquid immobilized in a wick 194. The preferred electrolyte in this implementation is a liquid base solution, such as an aqueous acid or salt solution. The reservoir serves to supply the wick with electrolyte over the life span of the sensor. Preferably, the housing in this instance is made of a molded plastic material. In specific instances, the electrode assembly is secured to the housing by an adhesive, or by a press or snap fit. Electrical connections for external circuitry can be made directly on the top side of the electrode assembly.

Figure 13:
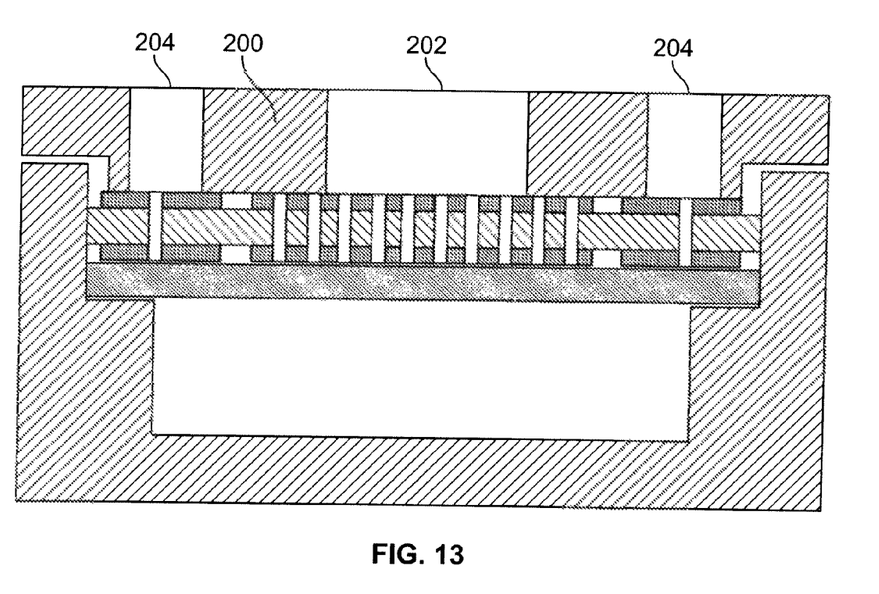

Referring now to FIG. 13, in yet another alternative sensor design, the housing shown in FIG. 12 uses a lid 200 to compress the electrode assembly onto the housing. The lid is preferably made of a molded plastic and has an opening 202 for gas access to the working electrode, and additional openings 204 for electrical connections. A filtering material, such as activated charcoal, may be placed in and/or over the opening 202 so that interfering gases may be filtered out. Additional dust filters, or flow restriction membranes may be placed over opening 202 to provide enhanced stability to the current output.

What is claimed is:

1. A method of making an electrochemical gas sensor, the method comprising:
   selecting a self-supporting pre-form comprising a solid agglomerated continuous conductive material, the pre-form comprising a working electrode device region and a counter electrode device region and a reference electrode device region, wherein each device region comprises two pre-electrode regions in electrical communication spaced apart in a first direction and extending across the pre-form in a second direction; and
   forming a plurality of apertures in the self-supporting pre-form to provide a porous working electrode device region; and
   connecting the device regions by an electrolyte on the back side of the pre-form; and
   forming an insulating material comprising a polymeric material about each device region in a manner that the insulating material fills spacings defined in the first direction between the three electrode device regions; and
   forming one or more apertures in the insulating material at the working electrode in a manner to allow a gas to pass through to the working electrode; and
   severing electrical connection of the pre-form into discrete spaced apart working, counter, and reference electrodes carried by the insulating material to provide an electrode assembly; and
   enclosing the electrode assembly in a molded plastic enclosure in a manner that external electronic circuitry can be connected directly outside the enclosure, and
   protecting the front side of the enclosure by a gas permeable membrane to allow gases to pass into the enclosure for easy detection, while keeping out liquids, such as water, that could damage the electrode assembly, and
   protecting the backside of the enclosure that includes the electrolyte in chemical communication with each electrode with a gas impermeable cover.

2. The method of claim 1, wherein the forming of the insulating material about each device region is performed using injection molding.

3. The method of claim 1, wherein the pre-form is made by chemically etching or stamping a sheet of metal.

4. A method comprising: manufacturing an electrochemical gas sensor by the method of claim 1; and connecting external electronic circuitry directly to the electrode assembly to measure electrical output from the electrodes when a detectable species is present, as current proportional to the species concentration is produced in the external circuit.

5. A method comprising: manufacturing an electrochemical gas sensor by the method of claim 1; and connecting a third reference external electronic circuitry directly to the electrode assembly to improve stability of the electrical output, by maintaining a fixed potential.

* * * * *

UNITED STATES PATENT AND TRADEMARK OFFICE
CERTIFICATE OF CORRECTION

| | | |
|---|---|---|
| PATENT NO. | : 8,266,795 B2 | Page 1 of 1 |
| APPLICATION NO. | : 12/446896 | |
| DATED | : September 18, 2012 | |
| INVENTOR(S) | : Mark Wagner | |

It is certified that error appears in the above-identified patent and that said Letters Patent is hereby corrected as shown below:

In the Specification

Column 1, lines 7-8
The patent should be amended to include the following statement:

"This invention was made with Government support under contract no. W31P4Q-06-C-0216 awarded by Defense Advanced Research Projects Agency (DARPA). The Government has certain rights in the invention."

Signed and Sealed this
Twenty-fifth Day of March, 2014

Michelle K. Lee
*Deputy Director of the United States Patent and Trademark Office*